United States Patent
Pathak et al.

(10) Patent No.: US 6,479,079 B1
(45) Date of Patent: Nov. 12, 2002

(54) ANTICALCIFICATION TREATMENTS FOR FIXED BIOMATERIALS

(75) Inventors: Chandrashenkhar P. Pathak, Austin, TX (US); Mark A. Moore, Austin, TX (US); Richard E. Phillips, San Marcos, TX (US)

(73) Assignee: Sulzer Carbomedics Inc., Austin, TX (US)

( * ) Notice: Subject to any disclaimer, the term of this patent is extended or adjusted under 35 U.S.C. 154(b) by 0 days.

(21) Appl. No.: 09/459,429

(22) Filed: Dec. 13, 1999

(51) Int. Cl.⁷ ............................................... A61K 35/00
(52) U.S. Cl. ..................................... 424/520; 424/569
(58) Field of Search ................................ 435/40.5, 520, 435/569

(56) References Cited

U.S. PATENT DOCUMENTS

| | | | |
|---|---|---|---|
| 4,259,472 A | 3/1981 | Cattha et al. ................ | 528/72 |
| 4,323,358 A | 4/1982 | Lentz et al. ................ | 8/94.11 |
| 4,755,593 A | * 7/1988 | Lauren ........................ | 530/356 |
| 4,838,888 A | 6/1989 | Nashef ......................... | 623/2 |
| 4,976,733 A | * 12/1990 | Girardot ..................... | 623/11 |
| 5,098,960 A | 3/1992 | Frautschi ................. | 525/359.3 |
| 5,147,514 A | 9/1992 | Mechanic ............... | 204/157.68 |
| 5,215,541 A | 6/1993 | Nashef et al. ............... | 8/94.11 |
| 5,263,992 A | 11/1993 | Guire .......................... | 623/66 |
| 5,296,583 A | 3/1994 | Levy ........................... | 528/72 |
| 5,332,475 A | 7/1994 | Mechanic ............... | 204/157.68 |
| 5,412,076 A | 5/1995 | Cagnieu .................... | 530/356 |
| 5,436,291 A | 7/1995 | Levy et al. ................ | 524/706 |
| 5,447,536 A | 9/1995 | Girardot et al. ............ | 8/94.11 |
| 5,476,516 A | * 12/1995 | Seifter et al. | |
| 5,645,587 A | 7/1997 | Chanda et al. ............... | 623/11 |
| 5,697,972 A | 12/1997 | Kim et al. ..................... | 623/2 |
| 5,746,775 A | 5/1998 | Levy et al. .................. | 8/94.11 |
| 5,882,850 A | 3/1999 | Khor et al. .................... | 435/1 |
| 5,931,969 A | 8/1999 | Carpentier et al. .......... | 8/94.11 |
| 5,958,669 A | 9/1999 | Ogle et al. ................... | 435/1.1 |
| 6,027,530 A | 2/2000 | Quintero et al. .............. | 623/2 |
| 6,039,760 A | 3/2000 | Eisenberg .................... | 623/15 |
| 6,156,531 A | * 12/2000 | Pathak et al. | |

OTHER PUBLICATIONS

Baldwin, M., et al., "FE3+ Preatreatment Provides Sustained Inhibition Of Bioprosthetic Heart Valve Calcification",The 17th Annual Meeting of the Society for Biomaterials,May 1–5, 1991, p. 61.

Bernacca, G. M., et al., "Chemical Modification Of Bovine Pericardium And Its Effect On Calcification In The Rat Subdermal Model", Biomaterials 1992, vol. 13 No. 6.

Ishihara, T., et al., "Calcific Deposits Developing In A Bovine Pericardial Bioprosthetic Valve3 Days After Implantation",Circulation,vol. 63, No. 3, Mar. 1981, pp. 718–723.

Shoen, F. J., et al., "Biomaterial–AssociatedCalcification:Pathology,Mechanisms,And Strategies for Prevention",J. Biomed. Mater. Res.: Applied Biomaterials, vol. 22 A1, 1988, pp. 11–36.

Broom, N. D., "The Stress/Strain And Fatigue Behaviour Of Glutaraldehyde Preserved Heart–Valve Tissue",J. Biomechanics,1977, vol. 10, pp. 707–724.

Cao, H., et al., "Characterization Of Mechanical Properties Of Photooxidation Modified Bovine Pericardium",21st Annual Meeting of the Society for Biomaterials, Mar. 18–22, 1995, p. 82.

Carpentier,A., et al., "Biological Factors Affecting Long–Term Results Of Valvular Heterografts",Journal of Thoracic and Cardiovascular Surgery, vol. 58, No. 4, Oct.,1969, pp. 467–483.

Chanda, J., "Prevention Of Calcification Of Heart Valve Bioprostheses:And Experimenta Study In Rat", Ann Thorac Surg, 1995, vol. 60, pp. S339–S342.

Cheung, D. T., et al., "Mechanism Of Crosslinking Of Proteins By Glutaraldehyde II. Reactio With Monomeric And Polymeric Collagen",Connective Tissue Research, 1982, vol. 10, pp. 201–216.

Chvapil, M, et al., "Effect Of Collagen Crosslinking On The Rate Of Resorption Of Implanted Collagen Tubing In Rabbits",J. Biomed. Mater. Res., vol. 11, 1977, pp. 297–314.

Gendler, E., et al., "Toxic Reactions Evoked By Glutaraldehyde–Fixed Pericardium And Cardiac Valve Tissue Bioprosthesis",Journal of Biomedical Materials Research, vol. 18, 1984, pp. 727–736.

Girardot, M. N., et al., "Alpha–Aminooleic Acid, A New Compound, Prevents Calcification Of Bioprosthetic Heart Valves", The 17th Annual Meeting of the Society for Biomaterials, May 1–5, 1991, p. 114.

Girardot, M. N., et al., "Development Of The AOA Process As Antimineralization Treatment For Bioprosthetic Heart Valves", The 19th Annual Meeting of the Society for Biomaterials, Apr. 28–May 2, 1993, p. 266.

(List continued on next page.)

Primary Examiner—Jean C. Witz
(74) Attorney, Agent, or Firm—Timothy L. Scott

(57) ABSTRACT

A method for treating biomaterial is provided in which a biological tissue, typically after being cross-linked, is contacted with an anticalcification treatment solution under condition effective to render the biomaterial resistant to in vivo calcification upon implantation in a host animal. The anticalcification treatment solutions comprise higher alcohol solutions, a polyol solutions and/or a polar aprotic organic solvent solutions.

46 Claims, No Drawings

OTHER PUBLICATIONS

Girardot, M. N., et al., "Role of Glutaraldehyde In Calcification Of Porcine Heart Valves: Comparing Cusp And Wall",Journal of Biomedical Materials Research, vol. 29, 1995, pp. 793–801.

Girardot, M. N., et al., "Effect Of AOA On Glutaraldehyde–Fixed BioProsthetic Heart Valve Cusps And Walls: Binding And Calcification Studies", The International Journal of Artificial Organs, vol. 17, No. 2, 1994, pp. 76–82.

Goissis, G., et al., "The Chemical Protecting Group Concept Applied In Crosslinking Of Natural Tissues With Glutaraldehyde Acetals", Artificial Organs, vol. 22., No. 3, pp. 210–214.

Golomb, G., et al., "The Role Of Glutarladehyde–Induced Cross–Links In Calcification Of Bovine Pericardium Used In Cardiac Valve Bioprostheses",Am J Pathol 1987, vol. 127, pp. 122–130.

Gott, J.P et al., "Calcification Of Porcine Valves: A Successful New Method Of Antimineralization",Ann Thorac. Surg 1992, vol. 53, pp. 207–216.

Greene, T. W., et al., "Protection For The Carbonyl Group", *Protective Groups in Organic Synthesis*, 1991, pp. 175–223.

Khor, E., "Methods For The Treatment Of Collagenous Tissues For Bioprostheses", Biomaterials, vol. 18, 1997, pp. 95–105.

Levy, R. J., et al., "Bioprosthetic Heart Valve Calcification-:Clinical Features, Pathobiology,And Prospects For Prevention",Critical Reviews in Biocompatibility,vol. 2, Issue 2, 1986, pp. 147–187.

Levy, R. J., et al., "Inhibition By Diphosphonate Compounds Of Calcification Of Porcine Bioprosthetic Heart Valve Cusps Implanted Subcutanously In Rats", vol. 71, No. 2, Feb. 1985, pp. 349–356.

Magilligan, D. J., "The Future Of Bioprosthetic Valves", vol. XXXIV, Trans Am Soc Artif Intern Organs, 1988, pp. 1031–1032.

Moczar, M., et al., "Deterioration Of Bioprosthetic Heart Valves", ASAIO Journal 1994, pp. M697–M701.

Moore, M. A., et al., "Stabilization Of Pericardial Tissue By Dye–Mediated Photooxidation", Journal of Biomedical Materials Research, vol. 28, 1994, pp. 611–618.

Munro, M. S., et al., "Alkyl Substituted Polymers With Enhanced Albumin Affinity", vol. XXVII, Trans Am Soc Artif Intern Organs, 1981, pp. 499–503.

Myers, D. J., et al., "Biocompatibility Testing Of Stentless Heart Valves Treated With 2–Amino Oleic Acid, A New Antimineralization Agent", The International Journal of Artificial Organs, vol. 16, No. 6, 1993, pp. 453.

Nielsen, S., "Endocytosis In Proximal Tubule Cells Involves A Two–Phase Membrane–Recycling Pathway",Am. J. Physiol. vol. 264, No. 33, 1993, pp. C823–C835.

Nimni, M. E., "A Defect In The Intramolecular And Intermolecular Cross–Linking Of Collagen Caused By Penicillamine", The Journal of Biological Chemistry, vol. 243, No. 7, Apr. 10, 1968, pp. 1457–1466.

Nimni, M. E., et al., "Chemically Modified Collagen:A Natural Biomaterial For Tissue Replacement",Journal of Biomedical Materials Research, vol. 21, 1987, pp. 741–771.

Okoshi, T., et al., "A New Bioprosthetic Cardiac Calve With Reduced Calcification",ASAIO Transactions, 1990, vol. 36, pp. M411–M414.

Oster, G, et al., "Dye Sensitized Photooxidation",J. Am. Chem. Soc., Oct. 5, 1959, vol. 81, pp. 5095–5099.

Parnis, S. M., et al., "Acoustic Spectral Analysis Of An Electrohydraulic Artificial Heart", ASAIO Journal, Supplement to Jan.–Mar. 1995, vol. 41, No. 1, p. 9.

Schoen, F. J., et al, "Cuspal Components In Bioprosthetic Valve Calcification:Elucidation And Modification",Surgery for Heart Valve Disease, Proceedings of the 1989 Symposium, pp. 679–685.

Thoma, R. J., "Poly(Ether) Urethane Reactivity With Metal–Ion In Calcification And Environmental Stress Cracking-",Journal of Biomaterials Applications, vol. 1, Apr. 1987, pp. 449–486.

Thubrikar, M. J., et al., "Role Of Mechanical Stress In Calcification Of Aortic Bioprosthetic Valves", J. Thorac Cardiovasc Surg, vol. 86, 1983, pp. 115–125.

Vesely, I., et al., "The Hybrid Xenograft/autograft Bioprosthetic Heart Valve: In Vivo Evaluation Of Tissue Extraction",Ann Thorac Surg, 1995, vol. 60, pp. S359–S364.

Webb, C. L., et al., "AL+++Preincubation Inhibits Calcification Of Bioprosthetic Heart Valv Tissue In the Rat Subdermal Model." vol. XXXIV, Am Soc Intern Organs, 1988, pp. 855–859.

Wiebe, D., et al., "Glutaraldehyde Release From Vascular Prostheses Of Biologic Origin", Surgery, vol. 104, 1988, pp. 26–33.

Woodroof, F. A., "Use Of Glutaraldehyde And Formaldehyde To Process Tissue Heart Valves", Processed Tissue Valves, 1977, pp. 1–9.

Zilla, P, et al., "Improved Ultrastructural Preservation Of Bioprosthetic Tissue", J Heart Valve Dis, vol. 6, No. 5, Sep. 1997, pp. 492–501.

* cited by examiner

ANTICALCIFICATION TREATMENTS FOR FIXED BIOMATERIALS

BACKGROUND OF THE INVENTION

1. Field of the Invention

The present invention relates generally to the field of medical devices for implantation into humans. More particularly, the present invention concerns methods for processing biological materials for use as bioprosthetic implantable devices.

2. Description of the Related Art

Bioprostheses are devices derived from processed biological tissues to be used for implantation into humans. The development of such devices originated as an attempt to circumvent some of the clinical complications associated with the early development of the mechanical heart valve, and has since resulted in a rapid proliferation of bioprosthetic devices for a variety of applications. Examples of some of the bioprostheses currently used or under development include heart valves, vascular grafts, biohybrid vascular grafts, ligament substitutes, pericardial patches, and others.

The primary component of the biological tissues used to fabricate bioprostheses is collagen, a generic term for a family of related extracellular proteins. Collagen molecules consist of three chains of poly(amino acids) arranged in a trihelical configuration ending in non-helical carboxyl and amino termini. These collagen molecules assemble to form microfibrils, which in turn assemble into fibrils, resulting in collagen fibers. The amino acids which make up the collagen molecules contain side groups, including amine (NH2), carboxylic acid (COOH) and hydroxyl (OH) groups, in addition to the amide bonds of the polymer backbone, all of which represent sites for potential chemical reaction on these molecules.

Because collagenous tissues degrade rapidly upon implantation into a host recipient, it is necessary to stabilize the tissue if it is to be used for clinical applications. Chemical stabilization by tissue cross-linking, also known as tissue fixation, has been achieved using a variety of compounds. Most typically, chemical fixation has employed polyfunctional molecules having two or more reactive groups capable of forming irreversible and stable intramolecular and intermolecular chemical bonds with the reactive amino acid side groups present on the collagen molecules. The most widely used of these polyfunctional molecules is the five carbon molecule, glutaraldehyde, which has an aldehyde at each end of a linear aliphatic chain. The aldehyde groups of glutaraldehyde and other like molecules react under physiological conditions with the primary amine groups of collagen molecules to cross-link the material. Glutaraldehyde cross-linked tissue produced in this way exhibits increased resistance to enzymatic degradation, reduced immunogenicity, and increased stability.

Despite its widespread use, there are certain disadvantages associated with tissue cross-linking with polyfunctional aldehydes and other chemical cross-linking agents. For example, upon implantation, aldehyde fixed tissue is susceptible to the formation of degenerative calcific deposits. Pathologic calcification, e.g., the undesirable deposition of calcium phosphate mineral salts in an implanted tissue, may represent the predominant cause of failure of glutaraldehyde-fixed bioprosthetic devices (Golomb et al., 1987; Levy et al., 1986; Thubrikar et al., 1983; Girardot et al., 1995). The mechanism for pathological calcification of implanted tissue is not fully understood, but may be due to host factors, implant factors, and/or extraneous factors, such as mechanical stress. Additionally, there is some evidence to suggest that deposits of calcium may be related to devitalized cells, and, in particular, to cell membranes in which the calcium pumps ($Ca^{+2}$–$Mg^{+2}$ ATPase) responsible for maintaining low intracellular calcium levels are no longer functioning or are malfunctioning.

Detergent pretreatment with non-covalently linked detergents, such as sodium dodecyl sulfate (SDS), or covalently bound detergents, such as amino oleic acid, have been reported to reduce calcification of materials exposed to circulating blood (Gott et al., 1992). However, detergents can adversely affect tissue structure and/or properties, resulting in a diminution of the collagen denaturation temperature, or shrink temperature, which is an important measure of material strength, durability, and integrity. Moreover, use of detergents can result in local toxicity.

In another approach, U.S. Pat. No. 5,746,775 describes the treatment of glutaraldehyde pretreated tissue with lower alcohols (i.e., C1–C3 alcohols), in which the lower alcohol is present at greater than 50% by volume in an alcohol treatment solution. The method is reported to be useful in preparing tissue for implantation into a living being.

Despite previous attempts at providing biomaterials having resistance to calcification, there remains a need for alternative anticalcification approaches with improved efficacy and ease of use. There is, thus, a need for an effective method of imparting long-term anticalcification properties to bioprosthetic materials, e.g., tissues, that is not accompanied by deleterious effects and that incorporate anticalcification agents and/or treatments into existing protocols for the preparation of clinical-grade biomaterials. The present invention is directed to overcoming or at least reducing the effects of one or more of the problems set forth above.

SUMMARY OF THE INVENTION

According to one aspect of the present invention, there is provided a method for treating a biomaterial comprising contacting a biomaterial, such as a cross-linked animal tissue, with an anticalcification treatment solution. The anticalcification treatment solutions of this aspect of the invention include solutions comprised higher alcohols or polyols and polar aprotic organic solvents. The anticalcification treatment solutions are contacted with the biomaterial under conditions effective to reduce pathologic calcification of the biomaterial following implantation into a mammalian host. As illustrated herein, this reduction in calcification can be monitored, for example, by evaluating the calcium content of an implanted biomaterial treated with an anticalcification treatment solution of the invention compared with an implanted biomaterial not so treated. Preferably, this reduction in calcification will be greater than 50%, more preferably greater than 75%, and most preferably greater than 90%, compared with an implanted, untreated biomaterial.

The higher alcohol or polyol used in formulating the anticalcification treatment solution may be a linear or branched C4–C36 alcohol or polyol. In certain preferred embodiments of the invention, the higher alcohol or polyol will be selected from a C6–C18 alcohol or polyol, preferably from a C7–C9 alcohol or polyol. Typically, the higher alcohol or polyol comprises less than about 50% by volume of said anticalcification treatment solution. In some instances, however, it will be desired to use an anticalcification treatment solution wherein the higher alcohol or polyol comprises less than about 25% by volume of said anticalcification treatment solution, or even less than about 10% by volume of said anticalcification treatment solution. The anticalcification treatment solution of the present invention may further comprise at least one organic solvent selected from, for example, C1–C3 alcohols. Moreover, the anticalcification treatment solution can also comprise water or an aqueous solvent.

Polar aprotic organic solvents useful in formulating the anticalcification treatment solutions of the present invention will preferably have dielectric constants greater than about 20, more preferably greater than about 30, and they will possess some degree of water solubility. Polar aprotic organic solvents useful in this aspect of the invention include, for example, N-alkyl pyrolidinones and N-alkyl amides, in which the alkyl group or groups comprise branched or linear alkyl chains having from about 1 to 10 carbon atoms. Illustrative solvents of this class include N-methyl pyrolidinone, N,N-dimethylacetamide, N,N-dimethylformamide, N,N-dimethylpropionamide, and the like.

In a further aspect of the present invention, there is provided a method for treating an aldehyde cross-linked animal tissue by forming an anticalcification treatment solution comprised of at least one organic solvent and from about 0.1% to about 25% by volume of a C6–C18 alcohol or polyol, and contacting the anticalcification treatment solution with the aldehyde cross-linked biomaterial under conditions effective to reduce pathologic calcification of the biomaterial following implantation into a mammalian host. As described above, an anticalcification treatment solution of the invention may contain one or more organic solvents and may further comprise water or a compatible aqueous solvent system. In one illustrative embodiment of this aspect of the invention, an organic solvent is present at about 35% to about 49% by volume of said anticalcification treatment solution, the remainder being comprised of said water or aqueous solvent. In this embodiment, it is preferred that the water or aqueous solvent is present at greater than about 50% by volume of said anticalcification treatment solution.

In yet a further aspect of the present invention, there is provided a method for treating an aldehyde cross-linked mammalian tissue by providing an anticalcification treatment solution comprised of about 0.1% to about 25% by volume of a C6–C18 alcohol or polyol, about 25% to about 99% by volume of an organic solvent selected from a C1–C3 alcohol, the remaining volume, if any, being comprised of water or an aqueous solvent; and contacting the anticalcification treatment solution with an aldehyde cross-linked biomaterial for a duration effective to reduce pathologic calcification of the biomaterial following implantation into a mammalian host. One illustrative embodiment of this aspect of the invention employs an organic solvent that is present at about 35% to about 45% by volume of the anticalcification treatment solution and a higher alcohol or polyol that is present at about 1% to about 10% by volume of the anticalcification treatment solution.

In another aspect of this invention, a method is provided for treating a biomaterial, comprising contacting an aldehyde-cross-linked biomaterial with an anticalcification treatment solution comprised of N-methyl pyrolidinone, N,N-dimethylacetamide, N,N-dimethylformamide and/or N,N-dimethylpropionamide under conditions effective to reduce pathologic calcification of the biomaterial following implantation into a mammalian host.

In another aspect of this invention, a method is provided for treating a biomaterial, preferably a cross-linked animal tissue, by contacting a biomaterial with an anticalcification treatment solution at a temperature between about 30° and 60° C. for a duration and under conditions effective to reduce pathologic calcification of the biomaterial following implantation into a mammalian host. The anticalcification treatment solutions comprise between about 10% and about 50% by volume, preferably between about 25% and 50% by volume, of a C1–C3 alcohol, such as methanol, ethanol, propanol, or isopropanol, the remaining volume being comprised of water or an aqueous buffer, such as HEPES.

DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The term "biomaterial" is used herein to refer generally to collagen-containing, biologically-derived materials. For example, various types of implantable biological tissues derived from numerous animal sources and parts of the anatomy can be used as biomaterials in accordance with this invention. The tissue can be derived, for example, from animal sources such as human, bovine, porcine, equine, sheep, kangaroo, rabbit, and others. Illustrative examples of animal tissues used in accordance with the present invention include, without limitation, heart valves, particularly porcine or bovine heart valves; aortic roots, walls, and/or leaflets; pericardium; connective tissue-derived materials such as dura mater; homograft tissues such as aortic homografts and saphenous bypass grafts; tendons; ligaments; skin patches; arteries; veins; and the like, Of course, other biologically-derived materials that are known as being suitable for in-dwelling uses in the body of a living being are also within the contemplation of the invention. For some applications, it may be desired to manipulate the biomaterial in some manner so as to provide it in a particular form or shape, for example using metallic stents prior to the treatments described herein. In this way, the biomaterial may be cross-linked and/or alcohol treated in the particular three-dimensional geometric configuration of the bioprosthesis to be implanted.

Typically, the biomaterial treated according to this invention is comprised of a biomaterial that has been fixed/cross-linked by treatment with one or more chemical cross-linking agents or other treatments that effect cross-linking. These can include, for example, treatments with polyfunctional aldehydes, polyfunctional epoxides, photoxidation and/or any other cross-linking agents or treatments that promote reactions between carboxylic acid and amine groups, such as N-(3-Dimethylaminopropyl)-N'-ethylcarbodiimide hydrochloride (EDC). Of course, the anticalcification treatments of this invention are preferably used in conjunction with cross-linking agents or treatments that increase the propensity of a biomaterial to calcify following implantation into a living host.

In one embodiment of the invention, the biomaterial is one that has been cross-linked by treatment with a monofunctional aldehyde, a polyfunctional aldehyde, or some combination thereof. A "monofunctional aldehyde" refers to a molecule containing a single aldehyde functionality, such as formaldehyde, while "polyfunctional aldehyde" refers to a molecule that contains two or more aldehyde functionalities. The other constituents present on the monofunctional or polyfunctional aldehyde are not critical provided they do not adversely effect the ability of the aldehyde groups to be collagen-reactive, and thereby capable of producing cross-linked biological tissues. Examples of monofunctional and polyfunctional aldehydes commonly used in biomaterial fixation methods for producing cross-linked biomaterials include aldehyde compounds that contain an aliphatic component comprising a linear or branched, saturated or unsaturated aliphatic chain having from about 2 to about 36 carbon atoms. Most preferably, cross-linking processes employ the use of a polyfunctional aldehyde having from 2 to about 10 carbon atoms, such as the linear five-carbon alkyl dialdehyde, glutaraldehyde.

As used herein, the terms "aldehyde fixed biomaterial" or "aldehyde cross-linked biomaterial" refers to biomaterial that has been treated with one or more monofunctional and/or polyfunctional aldehyde compounds. The techniques and coriditions for treating biomaterials with aldehyde-containing cross-linking agents are well known and are readily available to the skilled individual in the art (for example, see Zilla et al.). In these processes, a biomaterial is typically contacted with an aldehyde solution for a duration and under conditions effective to result in the desired degree of cross-linking of collagen and other cellular proteins within the tissue. Procedures for monitoring the progress and/or completion of the cross-linking reaction are also well known. For example, the degree of cross-linking of a treated tissue can be monitored by evaluating its shrinkage temperature and/or the quantity of extractable protein present in the material.

The skilled individual in this art will recognize that the duration of the cross-linking reaction according to this invention is not critical so long as the biomaterial and the cross-linking agent remain in contact for a time sufficient to allow cross-linking to occur. Time of treatment will of course vary depending on the type of biomaterial being treated, the particular aldehyde used and/or the concentration of the aldehyde in the cross-linking solution. Typically, the length of the reaction will be from about one minute to several days. However, the time of treatment should not be so long as to adversely effect the cross-linked biomaterial. Cross-linking times of several days or more are not uncommon. However, the biomaterial can also be treated for shorter periods as well, e.g., from about one minute to about twelve hours, or for about one hour to about six hours, provided the desired degree of cross-linking is achieved.

The reaction temperatures and/or pressures employed in a typical cross-linking reaction are not critical and can include essentially any conditions that are effective for allowing the cross-linking reaction to occur while not adversely compromising the progression of the reaction or the integrity of the biomaterial being treated. Identification of optimal temperature and pressure conditions for a particular implementation of the present invention can be readily determined by the skilled individual in this art. Generally, the cross-linking reaction can be carried out at an ambient temperature, or at any other convenient temperature that does not substantially exceed the tissue denaturation temperature of about 62° C. Thus, reaction temperatures may be selected from a temperature range from about 0° C. to about 60° C., preferably from about 20° C. to about 50° C. Although the pressure for a typical reaction generally ranges from about 2 mm Hg to about 6 mm Hg, suitable pressures may be as high as 100 mm Hg, or more, if desired.

After the biomaterial is cross-linked in this manner, the tissue is optionally washed/rinsed, and is contacted with an anticalcification treatment solution. The anticalcification treatment solutions of the present invention include solutions comprised of higher alcohols, polyols (i.e., organic molecules containing two more alcohol functionalities), polar aprotic solvents, such as N-methyl pyrolidinone, and solutions comprised of less than about 50% by volume of one or more lower (C1–C3) alcohols.

Therefore, according to one embodiment of the present invention, the anticalcification treatment solutions is comprised of one or more higher alcohols or polyols (e.g., a C4 to C36 alcohol or polyol). The higher alcohol or polyol will typically be an aliphatic linear or branched alcohol or polyol, and may contain additional chemical moieties or substituents provided they do not unacceptably interfere with the anticalcification effects described herein. In one illustrative embodiment of the invention, the higher alcohols used to formulate and anticalcification treatment solution are primary, secondary or tertiary alcohols selected from linear or branched C6–C18 aliphatic alcohols, such as hexanol, heptanol, octanol, nonanol, etc., or linear or branched C6–C18 polyols selected from 1,2-octanediol (also sometimes referred to as 1,2-dihydroxyoctane), 1,8-octanediol, 1,10-decanol, 1,10-dodecanol, 1,2-dihydroxydecane and 1,2-dihydroxydodecane.

In certain illustrative embodiments of the invention, the higher alcohols or polyols are present at less than about 50%, less than about 25%, or less than about 10%, by volume of the anticalcification treatment solution, the remainder being comprised of an organic solvent. Thus, in addition to the higher alcohols and polyols described above, the anticalcification treatment solution of the present invention may further contain one or more organic solvents. The organic solvents used in accordance with the present invention are preferably selected from those that do not have deleterious effects on the tissue being treated or on the anticalcification effects achieved by use of the anticalcification treatment solution. The organic solvents should be capable of adequately dissolving the higher alcohol or polyol to form a homogeneous anticalcification treatment solution. Organic solvents that can improve, enhance, or otherwise facilitate the anticalcification effects of the higher alcohols or polyols of this invention are, of course, particularly preferred. Organic solvents useful in accordance with this embodiment include lower alcohols (e.g., C1–C3 alcohols), acetone, ethyl acetate, ethyl lactate, 1,4-butanediol, polyethylene glycol, and the like.

Anticalcification treatment solutions according to certain embodiments of the invention comprise one or more higher alcohols and/or polyols in a preferably homogeneous mixture with one or more organic solvents. For example, particularly illustrative alcohol treatment solutions comprise from about 0.1% to about 25% by volume of one or more higher alcohols or polyols, with substantially all of the remainder of said solution being comprised of organic solvent. Additional illustrative anticalcification treatment solutions comprise from about 0.1% to about 10% by volume of one or more higher alcohols or polyols, with substantially all of the remainder of the solution being comprised of organic solvent.

Alternatively, the one or more higher alcohols or polyols of the anticalcification treatment solution may be formulated in an aqueous solvent system, e.g., with water or with any of a variety of aqueous buffer systems, or may be formulated in a mixture of an aqueous solvent system and one or more organic solvents. Some higher alcohols and polyols may exhibit poor solubility in aqueous based systems, but have greater solubility in many organic solvents. Thus, in embodiments which employ an aqueous based solvent systems, it will in some instances be preferred that one or more organic solvents is also employed in an amount at least sufficient to dissolve the higher alcohol or polyol to provide a homogeneous, i.e., substantially single-phase, anticalcification treatment solution.

Therefore, in additional embodiments of the invention, anticalcification treatment solutions are comprised of about 0.1% to about 25% by volume of one or more higher alcohols or polyols, about 25% to about 49% by volume of one or more organic solvents, with substantially all of the remainder of said solution being water or an aqueous based solution. Further embodiments of the invention provide anticalcification treatment solution comprised of about 0.1% to about 10% by volume of one or more higher alcohols or polyols, about 35% to about 45% by volume of one or more organic solvents, with substantially all of the remainder of said solution being water or an aqueous based solution.

In another embodiment of this invention, the anticalcification treatment solution is comprised of one or more polar aprotic solvents. Such solvents can include, for example, N-alkyl pyrolidinones and N-alkyl amides, in which the alkyl group or groups comprise linear or branched alkyl chains having from about 1 to 10 carbon atoms. Illustrative solvents of this type include N-methyl pyrolidinone, N,N-dimethylacetamide, N,N-dimethylformamide, N,N-dimethylpropionamide, and the like.

Particularly preferred polar aprotic solvents include those having some degree of water solubility and/or those with high dielectric constants, for example having dielectric constants greater than about 20, preferably greater than about 30.

In yet another embodiment of the invention, lower (C1–C3) alcohol treatment solutions, comprising less than 50% by volume of the lower alcohol, preferably between about 25% and 50%, are also suitable as anticalcification treatment solutions. Whereas prior anticalcification treatment attempts using lower alcohol solutions such as these have been unsuccessful, it has now been found that significant anticalcification effects can indeed be achieved by contacting a biomaterial with a lower alcohol treatment solution at a temperature in the range of about 30° C. to about 60° C., preferably between about 35° C. and 45° C. These treatment temperatures improve the efficacy of the anticalcification treatment solutions of this embodiment, possibly by facilitating the diffusion and penetration of the lower alcohols into the biomaterial. Preferably, the treatment according to this embodiment is accompanied by agitation of the anticalcification treatment solution while it is in contact with the biomaterial.

Cross-linked biomaterial is contacted with, or otherwise exposed to, an anticalcification treatment solution of the present invention for a period of time sufficient to render the biomaterial more resistant to in vivo pathologic calcification than a biomaterial not treated with the anticalcification treatment solution. The length of exposure in the embodiments described herein is illustrative only and can be varied by those of skill in the art while achieving a desired result. For embodiments of the invention wherein the biomaterial is immersed or soaked in a liquid anticalcification treatment solution, the exposure time will typically be in the range of about 1 hour to about 96 hours. For some biomaterials, excessive exposure to the anticalcification treatment solution may result in a decrease in the anticalcification effects, or may necessitate rehydration of the tissue.

The treatment procedure can be carried out at or near room temperature (e.g., about 25° C.) if desired. However, any temperature of convenience that is not deleterious to the biomaterial, for example about 4° C. to about 60° C., may also be used. As discussed above, it may indeed be desired and/or necessary in some embodiments to use an incubation temperature greater than room temperature in order to improve the efficacy of the treatment process, for example by increasing the rate and/or degree of diffusion and penetration of the anticalcification solutions into the biomaterial.

The biomaterial will typically be treated by contact with a liquid anticalcification treatment solution. However, other approaches could also be taken, such as vapor, plasma, and/or cryogenic application. Irrespective of the method of exposure, the time period should be sufficient to inhibit calcification, but not so long as to cause irreparable dehydration of the tissue by any of the constituents of the anticalcification treatment solution. In certain embodiments, the biomaterial is shaken or otherwise agitated during exposure to the anticalcification treatment solution in order to facilitate greater penetration of the constituents of the solution into the biomaterial. Shaking can be accomplished in any convenient manner, such as through use of an orbital shaker or shaker stand, or by manual agitation.

In some instances, it will be preferred to formulate an anticalcification treatment solution that is buffered in an aqueous solvent system, for example to a pH between about 6.0 and 8.0, preferably to a pH between about 7.0 and 7.6. Suitable buffers for use in this regard include buffers which have a buffering capacity sufficient to maintain a physiologically acceptable pH and do not cause any deleterious effects to the biomaterial or interfere with the treatment process being performed. Illustrative buffers include phosphate-buffered saline (PBS), organic buffers, such as N-N-2-hydroxyethylpiperzine-N'-2-ethanesulfonic acid (HEPES) and morpholine propanesulphonic acid (MOPS), and buffers which include borate, bicarbonate, carbonate, cacodylate, and the like. Many additional aqueous and other buffering systems suitable for use in the present invention will be apparent to the skilled artisan.

The biomaterial that has been treated with an anticalcification treatment solution may be rinsed prior to implantation or storage to remove any undesired and/or deleterious components produced or used in the biomaterial treatment protocol, such as cellular debris or aldehyde fragments from an aldehyde pretreatment. As used herein, the term "rinse" includes subjecting the biomaterial to a rinsing solution, including continuously or by batch processing, wherein the biomaterial is placed in a rinsing solution which may be periodically removed and replaced with fresh solution at predetermined intervals. During rinsing, the tissue is preferably shaken, or intermittently stirred, to ensure even distribution of the rinse solution. Illustratively, a rinse may comprise soaking the biomaterial in fresh rinsing solution which is replaced several times over a period of about an hour or less. Alternatively, the rinsing solution may be replaced at intervals of several hours or more over a longer rinse period, such as about 24 hours. Exemplary rinsing solutions include physiologically suitable solutions, such as water, saline, PBS, HEPES buffered saline, ringers lactate (pH 7.4), sodium bicarbonate (pH 7.4), tris (pH 7.4), imidazole (pH 7.4), and the like.

Subsequent to rinsing, the treated biomaterial is ready for implantation or may be sterilized and stored until use. Storage in standard glutaraldehyde solutions of the type typically used for long-term storage of clinical-grade bioprostheses may partially reverse the beneficial effects achieved by the treatment method of the present invention. Thus, it may be advantageous to store the treated biomaterial in an alcohol- or polyol-containing solution, such as an alcohol-glutaraldehyde solution, preferably under conditions which maintain calcification inhibition properties of the treated material.

In other embodiments of the invention, biomaterials which have been treated in accordance with the method of the invention are stored in an aldehyde-free environment. For example, treated tissue may be placed in sterile bags and subjected to sterilizing radiation, such as gamma-radiation. Of course, the treatment method of the present invention will be compatible with many other known sterilizing preservatives and/or techniques which are known by those of skill in the art.

In additional embodiments, the anticalcification treatment solution of the present invention may further comprise one or more additional anticalcification agents, including but not limited to, a soluble salt of a metallic cation, such as $Al^{+3}$ or $Fe^{+3}$, preferably in a concentration range of 0.001M to 0.1M. Water soluble aluminum salts, for example, which are suitable additional anticalcification agents for use in the practice of the present invention, include without limitation, aluminum chlorate, aluminum lactate, aluminum potassium sulfate, aluminum sodium sulfate, aluminum sulfate, aluminum nitrate, and aluminum chloride. Also, water-soluble ferric salts, such as ferric chloride, ferric nitrate, ferric bromide, ferric sodium edentate, ferric sulfate, and ferric formate, are also within the contemplation of the invention. Of course, any salt of aluminum, or iron, which is soluble in the solvent system of the treatment solution, may be used in the practice of the invention.

Although not wishing to be bound by this theory, the following may explain, at least in part, certain advantages realized by employing anticalcification treatment solutions in accordance with the present invention. In living tissue and cells, the typical extracellular calcium concentration is about 1 mM and the intracellular calcium concentration is about 0.1 □M. This large concentration gradient of calcium between the extracellular and intracellular regions is maintained by biochemical metabolic energy-dependent pumps across the plasma membranes of cells. Upon fixation, these biochemical forces are not active, and this results in a high concentration of calcium throughout the fixed tissue matrix. Plasma membranes and membrane bound organelles are rich in phospholipids, which provide phosphorous for calcium phosphate formation. In the in vivo environment, the high concentration of calcium in the fixed tissue coupled with a source of phosphorous from lipids may favor conditions for calcium phosphate crystallization. However, the constituents of the anticalcification treatment solutions used in accordance with this invention can be highly effective in penetrating the tissue matrix, interacting with, and possibly facilitating the removal of, phospholipids and other cellular debris from the cross-linked biomaterial, thereby interfering with the ability of such components to contribute to the crystallization process.

The following examples are provided to demonstrate certain illustrative embodiments of this invention. It should be appreciated by those skilled in the art that the techniques disclosed in the examples which follow represent those found by the inventors to function in the practice of the invention and thus can be considered to constitute examples of illustrative modes for its practice. However, those skilled in the art should, in light of the present disclosure, appreciate that many changes can be made in the specific embodiments which are disclosed and still obtain a like or similar result without departing from the spirit and scope of the invention.

EXAMPLES

Example 1

Treatment of Aldehyde-fixed Tissue with Higher Alcohols

Bovine pericardium was obtained fresh from the abattoir, trimmed to remove excess fat, and stored in a high osmolarity solution until use. Prior to fixation, the tissue was rinsed thoroughly in phosphate buffered saline (PBS) having a pH of 7.3–7.4. A 0.25% solution of glutaraldehyde was prepared by adding 2.5 ml of a 50% glutaraldehyde solution (Aldrich Chemical) to 500 ml using PBS. Fifteen 1 cm×1 cm samples of bovine pericardium tissue were added to the glutaraldehyde solution and the tube was stored at room temperature for 7 days.

In a sterile hood, glutaraldehyde fixed bovine pericardium pieces were washed with sterile PBS (3 washes, 10 minutes each). The samples were then immersed in a sterile filtered solution of 40% ethanol, 5% octanol, 55% water and treated for 24 hours at room temperature. The tissue was then washed with sterile PBS (3 washes, 10 minutes each), and in sterile filtered 45% ethanol in PBS for about 30 minutes. The samples were stored in 40 ml PBS for about 1 day prior to using them for rat implantation studies.

In a separate experiment, five 1 cm×1 cm samples of glutaraldehyde fixed bovine pericardium tissue (0.25% glutaraldehyde, 16 hrs) were treated with a solution comprised of 40% ethanol, 5% octanol and 55% water for 30 minutes. An additional 5 samples were treated in the solution for 24 hrs. After treatment, the samples were washed with PBS (30 ml×3) and stored in 45% ethanol. The samples were then analyzed to evaluate the presence of extractable proteins and to determine shrinkage temperatures.

Evaluation of Extractable Proteins and Shrinkage Temperatures

Cross-linking biological tissue results in less extractable protein within the material. Protein extraction assays were performed by extracting 10–20 mg of tissue with 10–20 □l of an extraction solution containing 50 mM Tris-HCl, 10% glycerol, 4% mercaptoethanol, 1% sodium dodecyl sulfate, 0.5M NaCl and 0.01% bromophenol blue. The extracted solution was then analyzed on a 4–20% acrylamide:bisacrylamide (37.5:1) Mini-PROTEAN II ready Gel (Biorad Inc).

The shrinkage temperatures of the treated tissues were also determined using standard differential scanning calorimetric analysis. Typically, 2–10 mg of tissue was heated at the rate of 10° C. per minute under nitrogen atmosphere. The onset of the endotherm observed at about 60–90° C. is conventionally attributed to a shrinkage transition, and was used as the shrinkage temperature. An increase in the shrinkage temperature is an indication that cross-linking has occurred.

The results of the extractable protein and shrinkage temperature determinations are summarized in Table 1 below:

TABLE 1

| Glutaraldehyde Treatment | Alcohol Treatment | Extractable Proteins | Shrink Temp. (° C.) |
|---|---|---|---|
| None | None | Yes | 66.3 |
| 0.25%, 24 hrs. | None | No | 79.2 |
| 0.25%, 24 hrs. | 40% EtOH 5% Octanol, 1 hr. | No | 79.9 |
| 0.25%, 24 hrs. | 40% EtOH 5% Octanol, 24 hr. | No | 80.2 |

From these results, it is clear that the treatment caused no degradation of the glutaraldehyde fixed tissue, as evidenced by the absence of extractable proteins. Moreover, neither the 1 hour nor the 24 hour treatments substantially effected shrink temperature values, indicating that the treatment did not alter physical properties of the glutaraldehyde fixed tissue.

Evaluation of Calcification Following In Vivo Implantation

Prior to implantation, the samples were rinsed 3 times for 3 minutes each in 500 ml containers of sterile PBS, accompanied by gentle agitation. Treated and untreated specimens were implanted subcutaneously using standard surgical procedures approximately 1 cm from the abdominal midline in 3 week old Sprague-Dawley rats. The implanted tissue was retrieved after 60 days.

Upon their removal, the tissue samples were processed using standard histological methods and stained with H&E, von Kossa and Masson's trichrome. von Kossa stain identifies calcification of the tissue. The extent of calcification by von Kossa stain was graded from 0 (none) to 5 (severe).

The calcium content of the retrieved samples was determined by hydrolyzing the samples under acidic conditions and analyzing the digested samples using standard inductively coupled plasma (ICP) emission spectrophotometry. Typically, about 0.5 g of the explanted tissue was dried, weighed and hydrolyzed under acidic conditions. The resulting digested sample was diluted with water and analyzed using an ICP spectrophotometer (Varian Inc.; Liberty 100/200 ICP-OCS).

The results of these experiments are summarized in Table 2 below:

TABLE 2

| GLUTARALDEHYDE TREATMENT | Alcohol Treatment | Calcium ($\mu$g/ mg dry tissue) | Average von Kossa Grading |
|---|---|---|---|
| 0.25%, 14 days | None | 201 | 5 |
| 0.25%, 14 days | 45% EtOH 24 hrs | 168 | 5 |
| 0.25%, 7 days | 40% EtOH 5% Octanol 24 hrs | 0.72 | 0 |

The tendency of glutaraldehyde fixed tissue to calcify in the rat model is well documented in the literature, an d t his was confirmed by our experiments. However, the glutaraldehyde fixed samples treated with an anticalcification treatment solution containing a higher alcohol (e.g., octanol) exhibited a significant reduction in calcification compared to those not treated. Samples treated with a 45% ethanol solution for 24 hours at room temperature showed values similar to the control samples.

Example 2
Treatment of Aldehyde-Fixed Tissue With 1,2-Octanediol And N-methyl Pyrolidinone In a sterile hood, pieces of glutaraldehyde-fixed bovine pericardium tissue (Mitroflow Inc.; Richmond, British Columbia, Canada) porcine cusp tissue (Labcor; Belo Horizonte, Brazil) and porcine wall tissue (Labcor Inc.) were transferred into sterile tubes containing 1,2-octanediol solutions (5% 152-octanediol (Aldrich Chemical), 40% ethanol and 55% 10 mM HEPES buffer). The tubes were transferred to a 37° C. incubator and maintained at 37° C. with gentle agitation for about 16 hours. After the treatment, the samples were transferred to solutions comprising 22% ethanol in 10 mM HEPES and stored for 14 days at 4° C. The final tissue to volume ratio for all treatments was approximately 27 ml/g.

For N-methyl pyrolidinone (NMP) treatments, pieces of glutaraldehyde-fixed bovine pericardium tissue (Mitroflow Inc.), porcine cusp tissue (Labcor Inc.) and porcine wall tissue (Labcor Inc.) were transferred into sterile tubes containing NMP. The tubes were incubated at room temperature for about 16 hours with occasional manual agitation. After the treatment, the tissue samples were transferred to 22% HEPES-buffered ethanol solutions and stored for 14 days at 4° C.

Evaluation of Calcification Following In Vivo Implantation

Samples treated with the 1,2-octanediol solutions and with NMP, as well as untreated samples of each tissue type, were provided to Charles Rivers Laboratories (Wilmington, Mass.) for implantation into rats. Seven rats per treatment group were analyzed. Prior to implantation, the tissue samples were rinsed for 3 minutes×3 in sterile PBS, accompanied by gentle agitation. The samples were implanted subcutaneously approximately 1 cm from the abdominal midline in 3 week old Sprague-Dawley rats and retrieved after 60 days of implantation. Unimplanted samples (one per tissue type per treatment) were used as unimplanted controls. After retrieval, the samples were analyzed for their calcium and phosphorus contents using a standard ICP methodology.

The results of these experiments are summarized below in Table 3.

TABLE 3

| Post-Fixation Treatment | Tissue Type | Calcuim ($\mu$g/mg tissue) | Phosphorus ($\mu$g/mg tissue) |
|---|---|---|---|
| None | Bovine Pericardium | 259.6 | 130.4 |
| None | Porcine Cusp | 348.0 | 174.8 |
| None | Porcine Wall | 199.2 | 102.2 |
| NMP | Bovine Pericardium | 8.0 | 3.4 |
| NMP | Porcine Cusp | 14.7 | 7.9 |
| NMP | Porcine Wall | 111.9 | 55.2 |
| 1,2-octanediol | Bovine Pericardium | 3.4 | 0 |
| 1,2-octanediol | Porcine Cusp | 44.1 | 21.9 |
| 1,2-octanediol | Porcine Wall | 106.4 | 53.0 |

Unimplanted controls had very low calcium and phosphorus levels (not shown). From the above table, however, it can be seen explanted tissue samples that had not had not been treated with an anticalcification treatment solution had very high levels of calcium and phosphorus. This was observed irrespective of the tissue type. On the other hand, explanted tissues that had been treated with either a 1,2-octanediol solution or with NMP had significantly reduced calcium and phosphorus levels. Interestingly, although the levels were reduced for all tissue types, the effect was most pronounced with bovine pericardium.

Explanted tissue samples were also sectioned, stained with H&E, and evaluated histologically for inflammation, vascularization and collagen organization. The 1,2-octanediol-treated samples, the NMP-treated samples, and the control samples had similar histological grading, indicating that the anticalcification treatments did not alter the biological response by the host animal.

Analysis of Extractable Proteins and Shrinkage Temperatures

For these experiments, bovine pericardium samples were placed in 0.25% solutions of glutaraldehyde in PBS where they remained at room temperature for about 7 days. The cross-linked tissues were then subjected to either 1,2-octanediol or NMP treatments, as described above. The treated samples were then analyzed for extractable proteins and to determine shrinkage temperatures.

In addition, enzymatic digestion assays were performed as follows. Tissue samples were digested after thermal denaturation for 10 minutes at 80° C. in 4 mg/ml pepsin (Sigma Chemical, St. Louis, Mo.) in 10 mM HCl for 4 hours at 37° C. Enzyme: tissue ratios (weight: wet weight) were 1:2500). Following centrifugation at 4° C. for 5 minutes at 13,000 rpm (30,000×g), reaction supernatants were used for gel electrophoresis.

The results of these experiments are summarized below in Table 4.

TABLE 4

| Glutaraldehyde Treatment | Post-Fixation Treatment | Extractable Protein Extraction Assay | Extractable Protein Shrink in after Digestion | Pepsin Temperature (° C.) |
|---|---|---|---|---|
| No | None | Yes | Yes | 61.8 |
| Yes | None | No | No | 87.0 |
| Yes | NMP | No | NO | 85.6 |
| Yes | 1,2-octanediol | No | NO | 86.0 |

These results demonstrate that for both anticalcification treatments (1,2-octanediol and NMP), there was no significant effect on shrinkage temperature when compared with untreated tissue, suggesting no significant change in the cross-linking status of the tissue had occurred as a result of the anticalcification treatments. Furthermore, both the treated and untreated samples failed to show any extractable proteins following the protein extraction and pepsin digestion assays, indicating that the anticalcification treatments did not adversely affect the biostability of the tissue.

Example 3
Treatment of Aldehyde-fixed Tissue with Lower Alcohol Solutions

In a sterile hood, pieces of glutaraldehyde-fixed bovine pericardium tissue (Mitroflow Inc.) were transferred into sterile tubes containing a 45% solution of HEPES-buffered ethanol (45% ethanol, 55% 10 mM HEPES buffer). The tubes were transferred to a 37° C. incubator and maintained at 37° C. with gentle agitation for about 16 hours. After the treatment, the samples were transferred to fresh solution of 45% HEPES-buffered ethanol and stored for 14 days at room temperature (~25° C.). The final tissue to volume ratio for all treatments was approximately 27 ml /g.

Evaluation of Calcification Following In Vivo Implantation

Samples treated with the 45% ethanol solution, as well as untreated samples of each tissue type, were provided to Charles Rivers Laboratories (Wilmington, Mass.) for implantation into rats. Seven rats per treatment group were analyzed. Prior to implantation, the tissue samples were rinsed for 3 minutes×3 in sterile PBS, accompanied by gentle agitation. The samples were implanted subcutaneously approximately 1 cm from the abdominal midline in 3 week old Sprague-Dawley rats and retrieved after 60 days of implantation. Unimplanted samples (one per tissue type per treatment) were used as unimplanted controls. After retrieval, the samples were analyzed for their calcium and phosphorus contents by ICP.

The results of these experiments are summarized below in Table 5.

TABLE 5

| Post-Fixation Treatment | Tissue Type | Calcuim (µg/mg tissue) | Phosphorus (µg/mg tissue) |
|---|---|---|---|
| None | Bovine Pericardium | 259.6 | 130.4 |
| 45% Ethanol | Bovine Pericardium | 3.4 | 0.0 |

This data demonstrates that the implanted tissue samples that did not receive any anticalcification treatment showed high levels of calcium and phosphorus. However, tissue samples treated with the ethanol solution showed a significant reduction in both levels. After the 60 day implantation period, unimplanted control samples had very low levels of calcium and phosphorus (not shown).

Thus, lower alcohol solutions having below 50% by volume of alcohol can reduce calcification under appropriate treatment conditions, for example by using elevated temperature to improve the efficacy of the treatment. Other solutions containing less than 50% by volume of a lower alcohol, for example methanol or isopropanol, could also be used.

The particular embodiments disclosed above are illustrative only, as the invention may be modified and practiced in different but equivalent manners apparent to those skilled in the art having the benefit of the teachings herein. More specifically, it will be apparent that certain agents which are chemically and/or physiologically related may be substituted for the agents described herein while the same or similar results would be achieved. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

REFERENCES

The following references, to the extent that they provide exemplary procedural or other details supplementary to those set forth herein, are specifically incorporated herein by reference.

U.S. Pat. No. 5,746,775
Girardot et al., J Biomed Mater Res (1995) 29: 793–801
Golomb et al., Am J Pathol (1987) 127: 122–130
Gott, J. P. et al.; Ann.Thorac.Surg.(1992) 53, 207–215
Levy et al., In: Williams D F, ed. CRC Critical Rev. in Biocompatibility, Vol. 2 (1986): 147–187
Thubrikar et al., J Thorac Cardiovasc Surg (1983) 86: 115–125
Zilla et al., J Heart Valve Dis (1 997) 6: 492–501

What is claimed is:

1. A method for treating a biomaterial comprising contacting a biomaterial with an anticalcification treatment solution, said anticalcification treatment solution comprising a compound selected from the group consisting of higher alcohols and polyols, wherein the higher alcohol or polyol comprises less than 50% by volume of said anticalcification treatment solution.

2. The method of claim 1, wherein the biomaterial is an animal tissue.

3. The method of claim 1, wherein the biomaterial is a cross-linked animal tissue.

4. The method of claim 1, wherein the biomaterial is an aldehyde cross-linked animal tissue.

5. The method of claim 1, wherein the higher alcohol or polyol is a linear or branched C4–C36 alcohol or polyol.

6. The method of claim 1, wherein the higher alcohol or polyol is a linear or branched C6–C18 alcohol or polyol.

7. The method of claim 1, wherein the higher alcohol or polyol is linear or branched C7–C9 alcohol or polyol.

8. The method of claim 1, wherein the higher alcohol is heptanol, octanol, or nonanol.

9. The method of claim 1, wherein the polyol is 1,2-octanediol, 1,8-octanediol, 1,10-decanol, 1,10-dodecanol, 1,2-dihydroxydecane or 1,2-dihydroxydodecane.

10. The method of claim 1, wherein the higher alcohol or polyol comprises less than about 25% by volume of said anticalcification treatment solution.

11. The method of claim 1, wherein the higher alcohol or polyol comprises less than about 10% by volume of said anticalcification treatment solution.

12. The method of claim 1, wherein the anticalcification treatment solution further comprises at least one organic solvent.

13. The method of claim 12, wherein the organic solvent is selected from a $C_1$–$C_3$ alcohol, acetone, ethyl acetate, ethyl lactate, 1,4-butaenediol or polyethylene glycol.

14. The method of claim 12, wherein the anticalcification treatment solution further comprises water or an aqueous solvent.

15. The method of claim 1, wherein the anticalcification treatment solution further comprises water or an aqueous solvent.

16. A method for treating a biomaterial comprising contacting a biomaterial with an anticalcification treatment solution, said anticalcification treatment solution comprising a polar aprotic organic solvent, wherein the contacting is performed for a period of time sufficient to render the biomaterial more resistant to in vivo pathologic calcification than a biomaterial not treated with the anticalcification treatment solution.

17. The method of claim 16, wherein the polar aprotic organic solvent has a dielectric constant greater than about 20.

18. The method of claim 17, wherein the polar aprotic organic solvent has a dielectric constant greater than about 30.

19. The method of claim 4, wherein contacting the aldehyde cross-linked biomaterial with said anticalcification treatment solution reduces the pathological calcification of the biomaterial following implantation into a mammalian host when compared to an aldehyde-cross-linked biomaterial that is not contacted with said anticalcification treatment solution.

20. A method for treating a biomaterial, comprising contacting an aldehyde cross-linked biomaterial with an anticalcification treatment solution, said anticalcification treatment solution comprising at least one organic solvent and from about 0.1% to about 25% by volume of a C6–C18 alcohol or polyol.

21. The method of claim 20, wherein the $C_6$–$C_{18}$ alcohol is a $C_7$–$C_9$ alcohol.

22. The method of claim 20, wherein the $C_6$–$C_{18}$ alcohol is heptanol, octanol or nonanol.

23. The method of claim 20, wherein the $C_6$–$C_{18}$ polyol is 1,2-octanediol, 1,8-octanediol, 1,10-decanol, 1,10-dodecanol, 1,2-dihydroxydecane or 1,2-dihydroxydodecane.

24. The method of claim 20, wherein the organic solvent is selected from $C_1$–$C_3$ alcohol, acetone, ethyl acetate, ethyl lactate, 1,4-butaenediol or polyethylene glycol.

25. The method of claim 20, wherein the organic solvent is ethanol.

26. The method of claim 20, wherein the anticalcification treatment solution further comprises water or an aqueous solvent.

27. The method of claim 26, wherein the organic solvent is present at about 35% to about 49% by volume of said anticalcification treatment solution, the remainder being comprised of said water or aqueous solvent.

28. The method of claim 26, wherein said water or aqueous solvent is present at greater than about 50% by volume of said anticalcification treatment solution.

29. The method of claim 20, wherein contacting the aldehyde cross-linked biomaterial with said anticalcification treatment solution reduces the pathological calcification of the biomaterial following implantation into a mammalian host when compared to an aldehyde-cross-linked biomaterial that is not contacted with said anticalcification treatment solution.

30. A method for treating a biomaterial, comprising contacting an aldehyde cross-linked animal tissue with an anticalcification treatment solution comprised of about 0.1% to about 25% by volume of a $C_7$–$C_9$ alcohol or polyol, about 25% to about 99% by volume of a $C_1$–$C_3$ alcohol, the remaining volume, if any, being comprised of water or an aqueous solvent; under conditions effective to reduce pathologic calcification of the tissue following implantation into a mammalian host.

31. The method of claim 30, wherein the $C_1$–$C_3$ alcohol is present at about 35% to about 45% by volume of the anticalcification treatment solution.

32. The method of claim 30, wherein the $C_7$–$C_9$ alcohol or polyol is present at about 1% to about 10% by volume of the anticalcification treatment solution.

33. The method of claim 30, wherein the $C_7$–$C_9$ alcohol is octanol.

34. The method of claim 30, wherein the $C_7$–$C_9$ polyol is 1,2-octanediol or 1,8-octanediol.

35. A method for treating a biomaterial, comprising contacting an aldehyde-cross-linked animal tissue with an anticalcification treatment solution comprising a polar aprotic organic solvent selected from the group consisting of N-methyl pyrolidinone, N,N-dimethylacetamide, N,N-dimethylformamide and N,N-dimethylpropionamide, under conditions effective to reduce pathologic calcification of the tissue following implantation into a mammalian host.

36. A method for treating a biomaterial, comprising contacting a cross-linked biomaterial with an anticalcification treatment solution at a temperature between about 30° and 60° C. under conditions effective to reduce pathologic calcification of the biomaterial following implantation into a mammalian host, said anticalcification treatment solution comprising between about 10% and about 50% by volume of a C1–C3 alcohol, the remaining volume being comprised of water or an aqueous buffer.

37. The method of claim 36, wherein the biomaterial is an animal tissue.

38. The method of claim 36, wherein the biomaterial is a cross-linked animal tissue.

39. The method of claim 36, wherein the biomaterial is an aldehyde cross-linked animal tissue.

40. The method of claim 36, wherein the $C_1$–$C_3$ alcohol is methanol, ethanol, propanol, or isopropanol.

41. The method of claim 36, wherein the aqueous buffer comprises HEPES.

42. The method of claim 36, wherein the $C_1$–$C_3$ alcohol comprises about 25 to about 50% by volume of the anticalcification treatment solution.

43. The method of claim 36, wherein the aldehyde cross-linked biomaterial is contacted with an anticalcification treatment solution at a temperature between about 30° C. and 60° C.

44. The method of claim 36, wherein the aldehyde cross-linked biomaterial is contacted with an anticalcification treatment solution for at least 12 hours.

45. The method of claim 12, wherein the polyol is 1,2-octanediol, the organic solvent is ethanol and the anticalcification treatment further comprises an aqueous buffer selected from the group consisting of phosphate-buffered saline, N-N-2-hydroxyethylpiperzine-N'-2-ethanesulfonic acid, morpholine propanesulphonic acid and buffers that include borate, bicarbonate, carbonate or cacodylate.

46. The method of claim 45, wherein the anticalcification treatment comprises 40% by volume ethanol; 5% by volume 1.2-octanediol and 55% by volume N-N-2-hydroxyethylpiperzine-N'-2-ethanesulfonic buffer.

* * * * *